(12) United States Patent
Friberg et al.

(10) Patent No.: US 7,219,666 B2
(45) Date of Patent: *May 22, 2007

(54) VENTILATOR

(75) Inventors: Harri Friberg, Buchs (CH); Jakob Däscher, Buchs (CH)

(73) Assignee: Event Medical Limited, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 10/893,421

(22) Filed: Jul. 15, 2004

(65) Prior Publication Data

US 2005/0000519 A1    Jan. 6, 2005

Related U.S. Application Data

(63) Continuation of application No. 09/958,520, filed as application No. PCT/IB00/00407 on Apr. 3, 2000, now Pat. No. 6,782,888.

(30) Foreign Application Priority Data

Apr. 7, 1999    (CH)    ........................ 652/99

(51) Int. Cl.
A62B 7/00    (2006.01)

(52) U.S. Cl. .............................. 128/204.18; 128/203.12

(58) Field of Classification Search ........... 128/204.18, 128/204.21, 204.23, 204.24, 203.12, 203.14, 128/205.11, 205.23, 205.24, 912, 202.27
See application file for complete search history.

(56) References Cited

U.S. PATENT DOCUMENTS

| 4,423,723 A | 1/1984 | Winkler et al. |
|---|---|---|
| 4,576,159 A | 3/1986 | Hahn et al. |
| 4,633,868 A | 1/1987 | Itoh et al. |
| 4,702,241 A | 10/1987 | Gravenstein et al. |
| 4,794,922 A | 1/1989 | DeVries |
| 4,825,860 A | 5/1989 | Falb et al. |
| 4,870,961 A | 10/1989 | Barnard |
| 4,881,541 A | 11/1989 | Eger, II et al. |
| 4,883,051 A | 11/1989 | Westenskow et al. |
| 4,905,688 A | 3/1990 | Vicenzi et al. |
| 4,986,268 A | 1/1991 | Tehrani |
| 4,989,597 A | 2/1991 | Werner |
| 4,991,576 A | 2/1991 | Henkin et al. |
| 5,119,810 A | 6/1992 | Kiske et al. |
| 5,307,795 A | 5/1994 | Whitwam et al. |
| 5,322,057 A | 6/1994 | Raabe et al. |
| 5,325,861 A | 7/1994 | Goulding |
| 5,368,019 A | 11/1994 | Latorraca |
| 5,520,172 A | 5/1996 | Obermayer |
| 5,549,105 A | 8/1996 | Bloch et al. |
| 5,570,682 A | 11/1996 | Johnson |
| 5,664,560 A | 9/1997 | Merrick et al. |
| 5,676,133 A | 10/1997 | Hickle et al. |

(Continued)

FOREIGN PATENT DOCUMENTS

EP    0 266 964    5/1988

(Continued)

*Primary Examiner*—Teena Mitchell
(74) *Attorney, Agent, or Firm*—Hunton & Williams, LLP

(57) ABSTRACT

A ventilator is disclosed which has a compact block made of plastic or metal and includes an electrical computer interface, in which rigid pipes and a gas supply container are integrated, resulting in a more compact device than conventional superstructures and improved therapy gas delivery and nebulization.

26 Claims, 3 Drawing Sheets

U.S. PATENT DOCUMENTS

| | | | |
|---|---|---|---|
| 5,678,539 A | 10/1997 | Schubert et al. | |
| 5,694,926 A | 12/1997 | DeVries et al. | |
| 5,832,917 A | 11/1998 | Särelä et al. | |
| 5,887,611 A | 3/1999 | Lampotang et al. | |
| 5,918,595 A | 7/1999 | Olsson et al. | |
| 5,927,275 A | 7/1999 | Löser et al. | |
| 5,934,274 A | 8/1999 | Merrick et al. | |
| 6,021,777 A | 2/2000 | Post et al. | |
| 6,041,777 A | 3/2000 | Faithfull et al. | |
| 6,089,229 A | 7/2000 | Bathe et al. | |
| 6,116,240 A | 9/2000 | Merrick et al. | |
| 6,186,142 B1 | 2/2001 | Schmidt et al. | |
| 6,213,120 B1 | 4/2001 | Block et al. | |
| 6,216,690 B1 | 4/2001 | Keitel et al. | |
| 6,279,574 B1 | 8/2001 | Richardson et al. | |
| 6,305,372 B1 | 10/2001 | Servidio | |
| 6,349,723 B1 | 2/2002 | Kock | |
| 6,400,996 B1 | 6/2002 | Hoffberg et al. | |
| 6,536,430 B1 | 3/2003 | Smith | |
| 6,543,449 B1 | 4/2003 | Woodring et al. | |
| 6,571,792 B1 | 6/2003 | Hendrickson et al. | |
| 6,739,334 B2 | 5/2004 | Valeij | |
| 6,782,888 B1 * | 8/2004 | Friberg et al. | 128/204.18 |
| 6,805,118 B2 | 10/2004 | Brooker et al. | |
| 6,837,260 B1 | 1/2005 | Kuehn | |
| 6,958,691 B1 | 10/2005 | Anderson et al. | |
| 7,040,318 B2 | 5/2006 | Däscher et al. | |
| 2002/0005197 A1 | 1/2002 | DeVries et al. | |
| 2002/0026940 A1 | 3/2002 | Brooker et al. | |
| 2003/0062045 A1 | 4/2003 | Woodring et al. | |
| 2003/0140922 A1 | 7/2003 | Dunlop | |
| 2003/0150456 A1 | 8/2003 | Wruck et al. | |
| 2003/0168062 A1 | 9/2003 | Blythe et al. | |
| 2003/0217749 A1 | 11/2003 | Dougill | |
| 2003/0230307 A1 | 12/2003 | DeVries et al. | |
| 2004/0089297 A1 | 5/2004 | Videbrink | |
| 2004/0099267 A1 | 5/2004 | Ahlmen et al. | |
| 2004/0144383 A1 | 7/2004 | Thomas et al. | |
| 2004/0172301 A1 | 9/2004 | Mihai et al. | |
| 2004/0250813 A1 | 12/2004 | Post et al. | |
| 2005/0055242 A1 | 3/2005 | Bello et al. | |
| 2005/0055244 A1 | 3/2005 | Mullan et al. | |
| 2005/0056281 A1 | 3/2005 | Snow | |
| 2005/0061323 A1 | 3/2005 | Lee et al. | |
| 2005/0065572 A1 | 3/2005 | Hartley et al. | |
| 2005/0109339 A1 | 5/2005 | Stahmann et al. | |
| 2005/0109340 A1 | 5/2005 | Tehrani | |
| 2005/0155602 A1 | 7/2005 | Lipp | |
| 2005/0229928 A1 | 10/2005 | Ivri et al. | |

FOREIGN PATENT DOCUMENTS

| | | | |
|---|---|---|---|
| EP | 0266964 | * | 5/1988 |
| EP | 0 769 304 | | 4/1997 |
| EP | 0 796 629 | | 9/1997 |
| WO | WO 97/19719 | | 6/1997 |
| WO | WO 99/27988 | | 6/1999 |

* cited by examiner

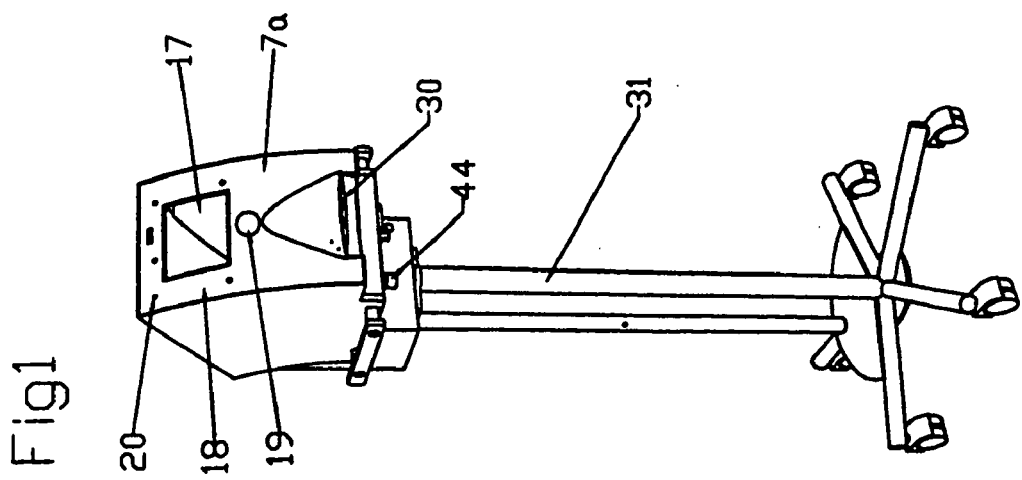
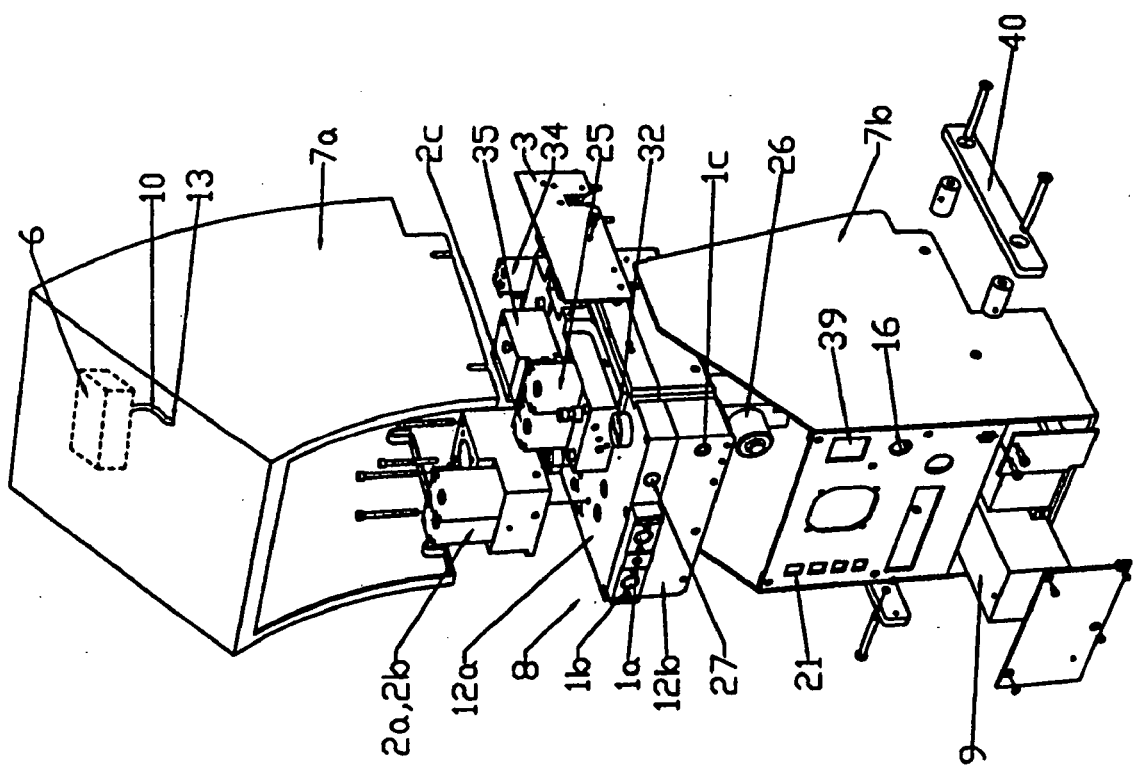

VENTILATOR

CROSS-REFERENCES TO RELATED APPLICATIONS

This is a Continuation Application of U.S. patent application Ser. No. 09/958,520 filed on Feb. 12, 2002, now U.S. Pat. No. 6,782,888, which is a national stage case from PCT/IB00/00407 filed on Apr. 3, 2000 and claims priority to Swiss Patent Application 652/99, filed on Apr. 7, 1999.

STATEMENT REGARDING FEDERALLY SPONSORED RESEARCH OR DEVELOPMENT

Not applicable.

BACKGROUND OF THE INVENTION

The invention refers to a ventilator.

TECHNICAL FIELD

Ventilators are used to either ventilate patients who have breathing difficulties or a loss of lung function, or they are used as gas mixing devices to condition the air inhaled by a patient. They therefore have ventilator gas connections, valves, controls for the valves and pressurised gas connections, to create gas pressure to inject air into the ventilating tubes or patient's lungs.

In operation the pressurised gas connections are often connected to a compressed air system, where the compressed air in the device operates a pneumatic pump, which transports the ventilator gases. However, the ventilator gases can be injected under pressure through the actual ventilator gas connections, meaning that the pressure required for ventilation is provided by the ventilator gases themselves. Ventilators do exist which can be attached to a compressor, which creates the necessary ventilator gas pressure when in operation and injects this into the ventilator.

Conventional ventilators therefore consist of a housing unit, which contains the gas supply container, valves, controls and possibly batteries as emergency power supply for the electrical valve controls as well. The housing also contains the ventilator gas connections and connections for the ventilating tubes mentioned above. The connections are connected to the valves and the gas supply container via tubes inside the device. As these tubes take up a certain amount of constructional volume and adequate space must be available to fit these tubes, conventional ventilators must be of a certain size.

SUMMARY OF THE INVENTION

The invention aims to reduce the constructional size of a ventilator. This task is solved by the distinctive features. The first step of the invention is to replace the tubes with rigid pipes. The second step of the invention is to integrate the tubes with the gas supply container, thus forming a compact block of plastic or metal. The invention then foresees the consequent integration or flange-mounting of the necessary valves and gas connections in/on this block. This produces a very compact design for the device.

Further developments for the invention, which could in principle also be used independently of the inventive concepts above, include the following particular points:

The integration of a compressor in the housing, where the compressor's pressure output could be connected to the block via a tube to allow vibration-free coupling of pressure between the compressor and the block.

Heated gas feeds, by using the heat generated by the compressor's activity to prevent the undesirable formation of condensation in the ventilator gas.

To achieve complete electrical self-sufficiency, where all electrically operated parts, which also includes the compressor, can be supplied with power from an internal battery. This battery should ideally be the main source of energy and should only be given a constant mains boost or charge via a charger where a mains feed is available. With this invention, disconnecting from the mains supply will not therefore interrupt ventilation in any way. This also dispenses with the need to connect a compressed gas supply by means of a gas bottle, which was an essential accompaniment previously. This makes it easier to transport a patient who is on a ventilator, as the ventilator can be simply disconnected from the mains and moved with the patient.

An integrated charger for the integrated battery with a preferred design, with which any AC mains voltages between 80 and 270 V can be fed without the operating staff having to make any settings on the power unit.

An integrated connector to connect the ventilator's electrics or electronics with an external DC source, e.g. the on-board power supply of a motor vehicle.

A display, which is integrated in the housing, and a control panel. The preferred design for the latter is a push-and-turn knob, which permits single-handed selection of fields and buttons on the display. The electronics for this are programmed such that the selected fields appear highlighted in colour, thus making it easier and safer to use. The preferred design has additional keys, which are used to trigger instant control operations and program steps or settings.

Electrical interfaces in the housing, constituting a computer port (RS 232 interface), a nurse call, etc.

Sensors, either connected to or integrated in the block, which permit a patient's breathing activities to be monitored and these values to be reproduced on the display. A software, parameterised by the sensors, also allows control of ventilation depending on the measured parameters.

Proximal flow sensors can be connected to detect the patient's own attempts to breathe in the immediate proximity of the patient and deliver this to the electronics of the device.

A special, new and independently applicable software, which allows forced sigh ventilation to be set for any interval and any pressure and/or volume values. Sigh ventilation of this sort is a known feature, however state-of-the-art devices only allow this sort of ventilation to be carried out in an unspecific way. Hence sigh ventilation can be activated or deactivated in conventional devices—for example, every hundredth breath is performed with 120% of the normal breath volume and the lungs of the patient are therefore overstretched a bit with every hundredth breath. It was previously believed that this was sufficient, as a comparable sigh breath frequency had been established for the average patient. The inventor has however discovered that the average sigh ventilation is not always ideal. This sort of ventilation may even be painful for a patient following a recent ribcage operation, for example. The way that this invention can be set means that personal consideration can be given to each patient's requirements.

BRIEF DESCRIPTION OF THE DRAWINGS

The figures describe a preferred design for the invention. This is an example and is not restrictive.

FIG. 1 A new type of ventilator, fully assembled and on a mobile stand;

FIG. 2 The same device in FIG. 1, showing the individual components;

DETAILED DESCRIPTION OF THE INVENTION

The Figures are described in general. Additional benefits and features of the invention, as well as additional preferred formations, arise from the description of the Figures.

Figure 4:
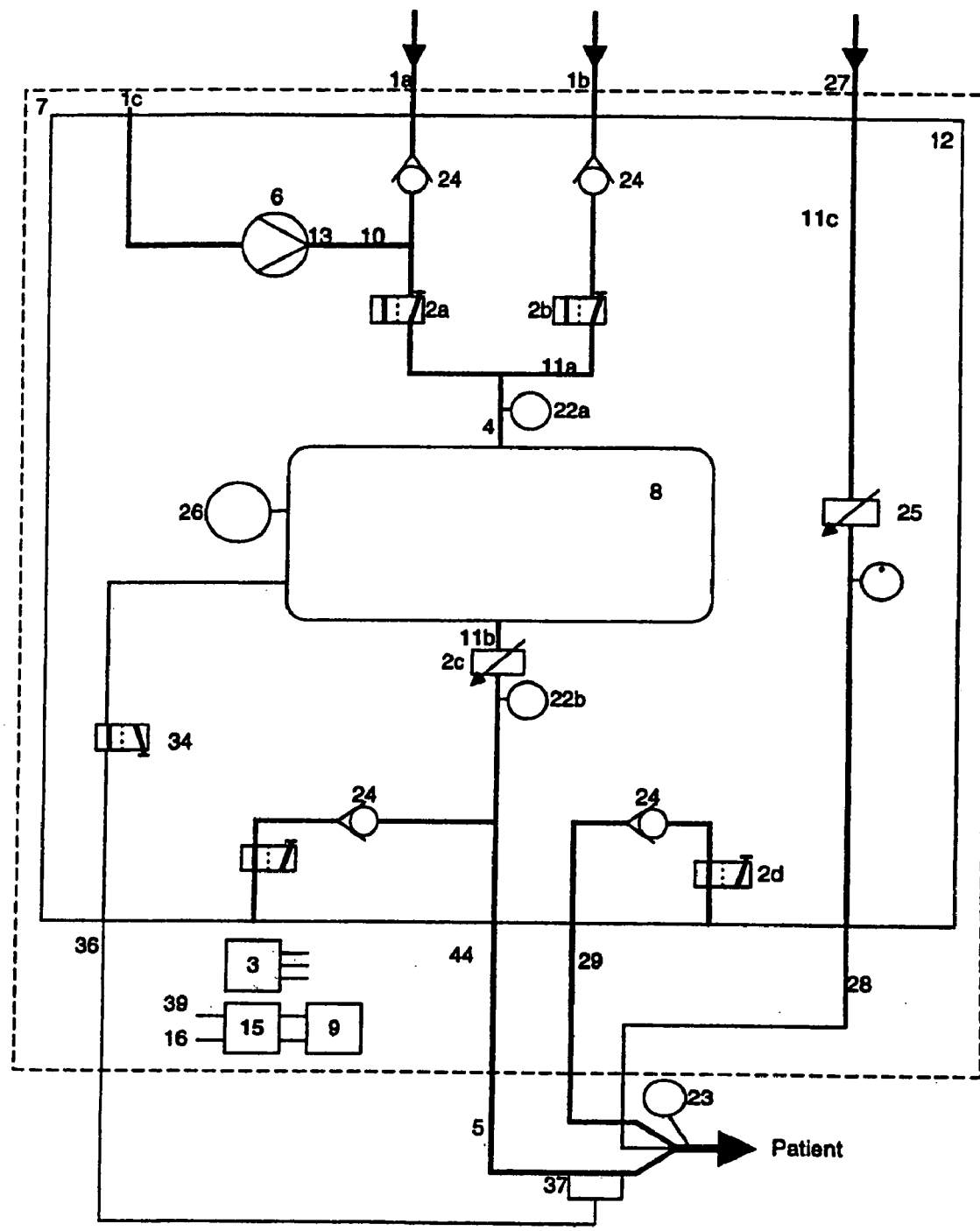
FIG. 4 A block diagram of the sample design.

The functionality and design of the preferred sample design can be seen in the block diagram in FIG. 4: on the input side you will see the gas connections—1*c* compressor input, 1*a* compressed air input, 1*b* ventilation gas input, e.g. oxygen input and 27 therapy gas input, e.g., for NO. The inputs are sighted on a block 12, which is found within the housing 7. Comprising input 1*c* leads to a compressor 6, which is connected via a flexible pipe 10 with a rigid pipe 11*a*, which forms a compressed air pipe 4 to a gas supply container 8. Pipe 11*a* is interrupted by a valve 2*a*, which either feeds or blocks the compressed air from the compressor or from the compressed air connection la to the gas supply container 8. A similar ventilation gas valve 2*b* feeds or blocks the ventilation gas passage to pipe 11*a* from ventilation gas connection 1*b* (in this case oxygen, for example).

Parallel to the pipe 11*a* a rigid pipe 11*c*, is fed through block 12 or is designed in the block wall in particular. Pipe 11*c* connects the therapy gas connection 27 to the therapy gas output 28. Pipe 11*c* is divided by a controllable therapy gas valve 25. This design was preferable to the known superstructures, where the therapy gas pipes and therapy gas control valves were housed separately to the ventilator and therefore needed additional expenditure on equipment. The advantages over the known design include not only a reduced amount of housing and reduced structural volume, but it is also simpler to operate and clearer in use.

The gas supply container 8 is equipped with an oxygen sensor 26. On the output side it is connected to the ventilator tube 5 via a rigid pipe 11*b*. The rigid pipe 11*b* has a controllable inspiration valve 2*c*. The pressure and/or flow is measured before as well as after the gas supply container 8 via integrated sensors 22*a* and 22*b*. A proximal flow sensor 23 permits measurement of the patient's own breathing performance.

To administer medication and humidity, a nebulizer pipe 36 is provided, which has a nebulizer valve 34 and nebulizer chamber 37. Various check valves 24 prevent loss of pressure if the connection tubes are disconnected. An expiration valve 2*d* terminates the expiration pipe 29. A ventilation tube 5, as well as a therapy gas output 28 if needed, run to the patient parallel to the expiration pipe 29.

The housing 7 also contains a control system or electronics 3, which are symoblically depicted and are especially connected to the electronically controlled valves and sensors. It also contains a battery or accumulator 9, which is powered from the charging equipment 15. A novel and preferential design of the charging equipment 15 allows it to connect to the DC power supply via a DC connection 16 on the one side and be charged with AC voltage of between 80 and 270 V via an AC connection 39 on the other side, without having to be set manually. Appropriate electronics are integrated in the charging equipment 15. The connection between battery 9 and charging equipment 15 is designed so that the battery receives a permanent charge all the time the charging equipment 15 is connected to the mains. If the external power supply fails, the system automatically switches to the internal battery. The control electronics comprises software that may be programmed via the control panel. The software operates to allow the setting of sigh ventilation for a patient, such as a selected time interval, repeatability and selected sigh pressure, selected sigh volume, and/or selected values of volume or pressure and gas mixture, such as mixture of air and NO.

Figure 3:
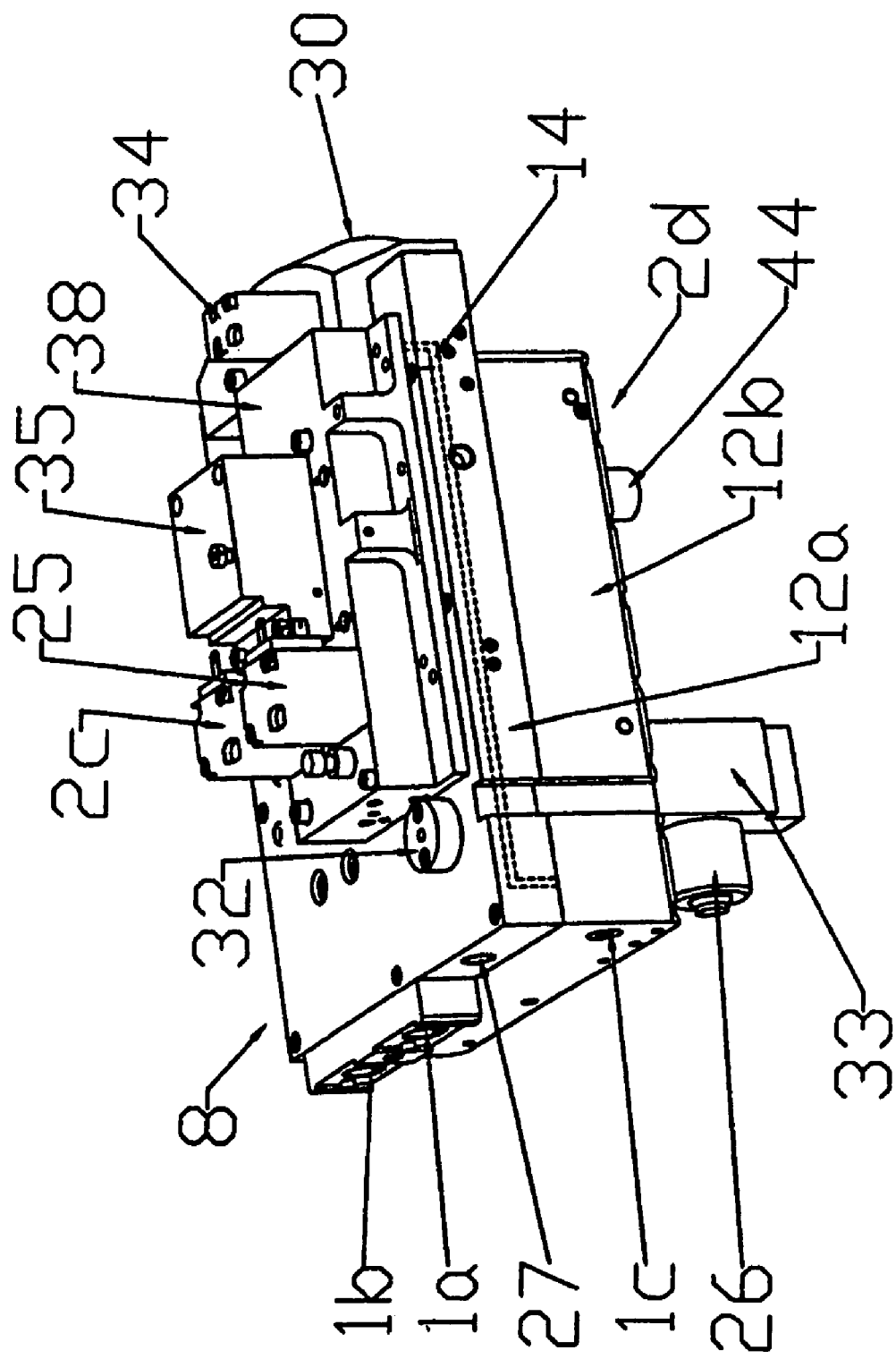
FIG. 3 The block feature of the invention as central part of FIG. 2.

In this sample design the block is divided into two—a lower section 12*b* and an upper section 12*a*. This is for assembly reasons and not essential. In the same way single piece or multi-piece blocks could be used for the invention. As can be seen in FIG. 3 the lower section 12*b* includes an oxygen block 33 with oxygen sensor 26 and expiration valve 2*d*. In service the lower section 12*b* is screwed tightly to the upper section 12*a* to form the gas supply container 8 on the inside.

In this invention the shell walls of the upper and lower sections 12*a* and 12*b* contain rigid pipes which represent the gas routes according to the block diagram in FIG. 4. A special pipe is represented by a broken line: gas deliverer 14 is a pipe which is connected to the compressor output 13. Compressed air leaving the compressor is warm when it is expelled. As this warm air has to travel a relatively long way through gas deliverer 14, this heat is released to block 12. This reduces the risk of condensation building up in the gas supply container 8. An alternative to the gas deliverer 14 shown here would be to use a longer, perhaps spirally rolled pipe inside the gas supply container 8 to access the compressor output 13.

Included in the upper section 12*a* are the compressed air and ventilator gas connections 1*a* and 1*b*, as well as therapy gas connection 27. It also carries a tank pressure control valve 32, the inspiration valve 2*c*, the therapy gas valve 25, and a safety block 35, which has a patient pressure relief valve and a patient suction relief valve. The last valves mentioned are equally located on valve block 38, which is designed as an integrated block and which incorporates the emergency valves and the devices for flow and pressure measurement in particular. The upper section 12*a* additionally carries a nebulizer valve 34 and the front connections 30.

FIG. 2 primarily shows the design in FIG. 3 when it is installed in housing 7, which is illustrated in two sections (7*a*, 7*b*) in this sample design. The compressor 6 with its flexible pipe 10 is symbolically illustrated. In the lower section of the housing 7*b* you can see a compartment with integrated battery 9, the electronics 3 and the location of the DC connection 16, an AC connection 39, as well as an interface 21 for a wide variety of connections, such as RS232, nurse call, etc.

The grips on the side 40 are used for transportation, as is the stand 31, which is shown in FIG. 1.

In FIG. 1 you can also see a display 17 and a keyboard 18 with push buttons 20 and a preferentially used push-and-turn knob 19. This makes it particularly easy to make the menu-controlled device settings, as mentioned in the introduction to the description.

What is claimed is:

1. A ventilator, excluding anaesthetizing equipment, comprising a closed breathing circuit, comprising:
    a housing forming an interior;
    a compact block;
    a gas supply container integrated in said block;

at least one ventilator gas connection for enabling a connection with an external gas supply;
at least one compressed air connection for enabling a connection with an external compressed air supply;
at least one valve;
a ventilating tube;
at least one connection for said ventilating tube;
gas pipes in the interior of said housing that connect said gas supply container with said at least one valve and said ventilator gas connection;
electrical control means including control electronics for controlling said at least one valve, said control electronics comprising sensing means for sensing at least one of the parameters including pressure, flow and oxygen;
wherein at least the majority of said gas pipes include rigid pipes and are integrated in said block together with said gas supply container, and
wherein said at least one valve and said at least one connection for said ventilating tube and said ventilator gas connection are integrated in said block.

2. The ventilator according to claim 1, wherein said electrical control means comprises an electrical computer interface formed to provide at least one of a nurse call and an RS232 connection.

3. The ventilator according to claim 1, wherein said electrical control means comprises an interface having a software download facility.

4. The ventilator according to claim 1, wherein the at least one valve comprises a compressed air valve and further comprising a ventilation gas valve both leading to the gas supply container integrated into the block, wherein the two valves control the mixture of gas into the gas supply container integrated into the block.

5. The ventilator according to claim 4, in which the control of the mixture is based on pressure inside the gas supply container integrated into the block.

6. The ventilator according to claim 4, wherein the maximum pressure inside the gas supply container integrated into the block is limited by a pressure control valve.

7. The ventilator according to claim 4, further comprising oxygen monitoring, incorporating an oxygen sensor integrated into the block.

8. The ventilator according to claim 1, further comprising a DC powered compressor having an output within the housing, said compressor being connected to said gas supply container via one of said gas pipes.

9. The ventilator according to claim 1, wherein the control electronics comprises software that is programmed via a control panel and allows setting sigh ventilation for a patient at a selected time interval, repeatability and selected sigh pressure.

10. The ventilator according to claim 1, wherein the control electronics comprises software that is programmed via a control panel and allows setting sigh ventilation for a patient at a selected time interval, repeatability and selected sigh volume.

11. The ventilator according to claim 1, wherein said breathing circuit comprises an internal compressor in said housing.

12. The ventilator according to claim 11, wherein the control electronics comprises software that is programmed via a control panel and allows setting ventilation for a patient at selected values of volume or pressure.

13. The ventilator according to claim 12, wherein said sensing means comprises at least two sensors that are integrated into the block.

14. The ventilator according to claim 12, wherein said control panel further comprises a removable top housing including a display.

15. The ventilator according to claim 1, wherein said at least one valve comprises a controllable valve, and said sensing means comprises a flow sensor and a pressure sensor for controlling the delivery of gas from said gas supply container integrated into said block via said controllable valve.

16. The ventilator according to claim 1, wherein measured parameters from said sensing means are used to control gas delivery to a patient.

17. The ventilator according to claim 1, wherein said breathing circuit comprises at least one of the following: a humidifier, and an inline nebulizer.

18. The ventilator according to claim 1, wherein said at least one valve comprises a compressor air valve or a ventilation gas valve, either of said valves being supplied via a one way check valve.

19. The ventilator according to claim 1, wherein one or more of an oxygen mixture and Nitric Oxide are usable as a supply gas.

20. The ventilator according to claim 19, wherein said supply gas is mixable with air and $O_2$ for delivery to the patient.

21. A ventilator, comprising a closed breathing circuit, comprising:
a housing forming an interior;
a compact block;
a gas supply container integrated in the block;
at least one ventilation gas input for enabling a connection with an external gas supply;
at least one compressed air input;
a ventilation gas valve;
a compressed air valve;
gas pipes in the interior of said housing that connect said gas supply container with the ventilation gas valve and with the compressed air valve;
electrical control means including control electronics for controlling at least one of the ventilator gas valve and the compressed air valve, the control electronics comprising sensing means for sensing at least one of the parameters selected from pressure, flow and oxygen;
wherein at least the majority of the gas pipes include rigid pipes and are integrated in the block together with the gas supply container, and
wherein both the ventilator gas valve and the compressed air valve are integrated in or on the block.

22. The ventilator according to claim 21, further comprising,
a nebulizer pipe connected to the gas supply container.

23. The ventilator according to claim 22, further comprising,
an output of the nebulizer pipe flowing through a nebulizer valve and into a nebulizer chamber.

24. The ventilator according to claim 21, further comprising,
a compressor in the housing wherein the compressor's pressure output is connected to the block through a tube.

25. A ventilator, comprising a closed breathing circuit, comprising:
a compact block;
a gas supply container integrated in the block;
at least one valve block integrated on the compact block with at least one valve flange-mounted thereon;
at least one ventilation gas input;

at least one compressed air input;
a ventilation gas valve;
a compressed air valve;
gas pipes in the interior of the compact block that connect said gas supply container with the ventilation gas valve and with the compressed air valve;
electrical control means including control electronics for controlling at least one of the ventilator gas valve and the compressed air valve;
wherein at least the majority of the gas pipes include rigid pipes and are integrated in the compact block together with the gas supply container, and wherein both the ventilator gas valve and the compressed air valve are integrated in or on the compact block or integrated in or on the valve block.

26. The ventilator according to claim 25, further comprising, an integrated charger for an integrated battery,
wherein the integrated charger is capable of being connected to a DC power supply and capable of being charged by an AC voltage.

* * * * *